US00PP15235P2

(12) United States Plant Patent
Bradford

(10) Patent No.: US PP15,235 P2
(45) Date of Patent: Oct. 12, 2004

(54) INTERSPECIFIC PLUM TREE NAMED 'PLUMSWEETTHREE'

(50) Latin Name: ***Prunus salicina*×(*Prunus salicina*× *Prunus armeniaca*)**
Varietal Denomination: Plumsweetthree

(76) Inventor: Lowell Glen Bradford, 12439 E. Savana Rd., Le Grand, CA (US) 95333

( * ) Notice: Subject to any disclaimer, the term of this patent is extended or adjusted under 35 U.S.C. 154(b) by 0 days.

(21) Appl. No.: 10/746,722

(22) Filed: Dec. 29, 2003

(51) Int. Cl.[7] ..... A01H 5/00
(52) U.S. Cl. ..... Plt./180
(58) Field of Search ..... Plt./180

(56) References Cited
U.S. PATENT DOCUMENTS

PP8,498 P 12/1993 Bradford

*Primary Examiner*—Kent Bell
*Assistant Examiner*—S B McCormack-Ewoldt

(57) ABSTRACT

The present invention relates to an interspecific plum tree, *Prunus salicina*×(*Prunus salicina*×*Prunus armeniaca*), and more particularly to a new and distinct variety broadly characterized by a medium size, vigorous, hardy, and self-unfruitful but productive tree. The fruit matures under the ecological conditions described during mid August, with first picking on Aug. 7, 2003. The fruit is uniformly large in size, two-tone red and yellow in skin color, semi-freestone in type, purely yellow in flesh color, firm in texture, very good in cold storage, and mildly acidic and very sweet in flavor, which is predominately plum with a hint of apricot.

1 Drawing Sheet

Botanical classification: Interspecific *Prunus salicina*× (*Prunus salicina*×*Prunus armeniaca*).
Variety denomination: 'Plumsweetthree'.

BACKGROUND OF THE VARIETY

In a continuing effort to improve the quality of shipping fruits, I, the inventor, typically hybridize a large number of peach, nectarine, plum, apricot, and cherry seedlings each year. I also grow a lesser number of open pollination seeds of each of these fruits. During my plant breeding career I have hybridized many plum trees using a variety of plum, apricot, and interspecific plum-apricot pollen. Some of these interspecific plum-apricot hybrids include 'Red Velvet' (U.S. Plant Pat. No. 7,011), 'Royal Velvet' (U.S. Plant Pat. No. 7,431), and a few unnamed interspecific trees that produce fruit of various skin and flesh colors, including pure yellow skin and flesh. Over the years I isolated about twenty trees of desirable plums and these interspecific trees at my home orchard near Le Grand, Calif. During the summer of 1997 I gathered fruit from one of these trees, an unnamed red plum that was an open pollinated seedling of 'Bradgreen' (U.S. Plant Pat. No. 8,498) plum. The seeds from this fruit were removed, cracked, stratified, germinated, and grown as seedlings on their own root in my greenhouse. Upon reaching dormancy that fall, they were transplanted as a group with the label "Red Plum (OP)" to a cultivated area of my experimental orchard at Bradford Farms near Le Grand, Calif. in Merced County (San Joaquin Valley). During the evaluation season of 2001, the present variety was selected as a single plant from the group of seedlings described above.

The present invention relates to a new and distinct variety of interspecific plum tree, which has been denominated varietally as 'Plumsweetthree'. The present variety exhibited several indications that it was probably a cross between the seed parent, an unnamed red plum, and an unnamed interspecific plum-apricot hybrid tree with pure yellow skin and flesh. Those traits included a red and yellow two-tone skin color, yellow flesh, and a plum taste with a hint of apricot flavor. Subsequent to origination of the present interspecific plum tree, I asexually reproduced it by budding and grafting in the experimental orchard described above, and such reproduction of plant and fruit characteristics were true to the original plant in all respects. The reproduction of the variety included the use of 'Nemaguard' (unpatented) rootstock upon which the present variety was compatible and true to type.

The present variety is similar to its seed grandparent, 'Bradgreen' (U.S. Plant Pat. No. 8,498), by being self-unfruitful and by producing fruit that is globose in shape, acidic and sweet in flavor, firm in texture, and matures in mid August, but is distinguished therefrom by blooming about ten days later and by producing fruit that is two-tone red and yellow instead of purely green in skin color, that is semi-freestone rather than clingstone in type, that is less susceptible to skin scuffing, and that has a unique plum with a hint of apricot flavor.

SUMMARY OF VARIETY

The present interspecific plum variety is characterized by a medium size, vigorous, hardy, and productive tree. Being self-unfruitful, the present variety requires cross pollination from another plum that blooms during the late season, such as 'Autumn Yummy®' (U.S. Plant Pat. No. 14,178). The fruit matures under the ecological conditions described during mid August, with first picking on Aug. 7, 2003. The fruit is uniformly large in size, two-tone red and yellow in skin color, semi-freestone in type, purely yellow in flesh color, firm in texture, very good in cold storage, and mildly acidic and very sweet. In flavor, which is predominately plum with a hint of apricot.

DRAWING

The accompanying photograph exhibits four whole fruits positioned to display the characteristics of the skin color and form, one fruit divided transversely to the suture plane to reveal the flesh and stone, and typical leaves.

DETAILED BOTANICAL DESCRIPTION

Referring now more specifically to the pomological characteristics of this new and distinct variety of interspecific plum tree, the following has been observed under the ecological conditions prevailing near Le Grand, Merced County (San Joaquin Valley), Calif., and was developed at the state of shipping ripe on Aug. 12, 2003, on the original tree during its sixth growing season. All major color code designations are by reference to the Inter-Society Color Council, National Bureau of Standards. Common color names are also used occasionally.

Tree

Size: Medium, reaching a height of 8' [2.4 m.] and a spread of 6' [1.8 m.] after six growing seasons utilizing typical dormant pruning.

Vigor: Medium, responding typically to irrigation and fertilization. The variety grows about 3' [0.9 m.] of surplus top-growth during the spring and summer. The plant should be grown on a standard commercial rootstock for production purposes.

Growth: Spreading and dense.

Form: Trained to a two leader V-shape by pruning.

Hardiness: Hardy with respect to central California winters.

Heat tolerance: Observed to perform adequately in typical central California climatic conditions, which typically include prolonged periods of heat.

Drought tolerance: Variety is developed for commercial orchards and requires regular irrigation.

Production: Productive, thinning usually necessary.

Fertility: Self-unfruitful, requiring cross pollination by a suitable late seasonal blooming plum or apricot. 'Autumn Yummy®' (U.S. Plant Pat. No. (14,178) was determined as one such pollinator in 2003.

Bearing: Regular bearer.

Trunk:

*Size.*—Medium, reaching a maximum diameter of 4⅜" [111 mm.] after the sixth growing season.

*Texture.*—Shaggy.

*Bark color.*—Dark grayish brown [62. d.gy.Br] with Light yellowish brown [76. l.yBr] crevices.

*Lenticels.*—Approximate number per square inch: 20. Color: Brownish orange [54. br.O]. Typical size: ⅛" to 7/16" [3.2–11.1 mm.].

Branches:

*Size.*—Diameter of limb is 2¼" [57.2 mm.] measured 12" above the primary fork.

*Texture.*—Smooth on first year wood, increasing roughness with age.

*Color.*—1st year wood topside: Moderate reddish brown [43. m.rBr]. 1st year wood underside: Brilliant yellow green [116. brill.YG]. Older wood: Moderate yellowish brown [77. m.yBr].

*Lenticals.*—Approximate number per square inch: 80. Color: Light orange yellow [70. l.OY]. Typical size: 1/32" to ⅛" [0.8–3.2 mm.].

Leaves:

*Size.*—Medium. Average length: 1¾" [45 mm.]. Average width: 4¼" [108 mm.].

*Arrangement.*—Alternate.

*Thickness.*—Medium.

*Form.*—Elliptical.

*Apex.*—Acuminate.

*Base.*—Acute with an average angle base angle of seventy-five degrees.

*Surface.*—Smooth.

*Color.*—Dorsal surface: Moderate olive green [125 m.OlG]. Ventral surface: Moderate yellow green [120. m.YG].

*Margin.*—Finely serrate.

*Venation.*—Pinnately net veined.

*Petiole.*—Average length: ⅝" [15.9 mm.]. Average thickness: 1/16" [1.6 mm.]. Color: Light yellow green [119. l.YG] with slight Grayish reddish orange [39. gy.rO] tinting.

*Stipules.*—Number: 2 per young leaf, up to 6 per growing tip. Average Length: ¼" [6.4 mm.]. Color: Light yellow green [119. l.YG].

*Glands.*—Average number: 1 to 4. Position: Usually alternate, located on petiole near the base of blade. Size: Small. Form: Globose. Color: Mostly Moderate reddish brown [43. m.rBr], some Brilliant yellow green [116. brill.YG].

*Leaf buds.*—Small, pointed to conic, Dark grayish yellowish brown [81. d.gy.yBr].

Flower buds:

*Hardiness.*—Hardy, with respect to central California winters.

*Diameter.*—Typically 3/16" [4.8 mm.] 1 week before bloom.

*Length.*—Typically ⅜" [9.5 mm.] 1 week before bloom.

*Form.*—Not appressed.

*Surface.*—Pubescent.

*Color.*—White [263. White].

Flowers: Perfect, complete, perigynous, usually a single pistil, typically twenty-eight or more stamens, five sepals and petal locations alternately positioned.

*Average flower diameter.*—13/16" [20.6 mm.].

*Number of petals.*—Five, no double blossoms observed.

*Petal shape.*—Oval.

*Petal margin.*—Somewhat wavy.

*Average petal diameter.*—⅜" [9.5 mm.].

*Average petal length.*—7/16" [11.1 mm.].

*Petal apex.*—Rounded.

*Petal base.*—Cuneate.

*Petal color.*—White [263. White].

*Anther color.*—Light yellow [86. l.Y].

*Stigma color.*—Light greenish yellow [101. l.gY].

*Sepal color.*—Light yellow green [119. l.YG] with Moderate purplish pink [250. m.pPk] tinting on the edges.

*Sepal length.*—5/32" [4.0 mm.].

*Sepal width.*—⅛" [3.2 mm.].

*Average pistil length.*—7/16" [11.1 mm.].

*Average stamen length.*—5/16" [7.9 mm.].

*Fragrance.*—Moderate.

*Pollen production.*—Average.

*Blooming period.*—Late compared with other varieties, about six days after 'Santa Rosa' (unpatented).

*Onset of bloom.*—One percent on Feb. 28, 2003.

*Date of full bloom.*—Mar. 9, 2003.

*Duration of bloom.*—One to two weeks, dependent on ambient temperature.

*Number per cluster.*—Average 3, up to 8 observed.

Fruit

Maturity when described: Firm ripe, Aug. 12, 2003.

Date of first picking: Aug. 7, 2003.

Date of last picking: Aug. 20, 2003.

Size: Uniform, medium.
*Average diameter axially.*—2 11/16" [68.3 mm.].
*Average diameter across suture plane.*—2 9/16" [65.1 mm.].
*Typical weight.*—6.0 ounces [170 grams].
Form: Somewhat variable, mostly globose with some elongated noses due to split stones caused by frost during the 2003 blooming season.
*Longitudinal section form.*—Oval.
*Transverse section through diameter.*—Elliptical.
Suture: A shallow groove extending from the base, around the side, and discontinuing at the pistil point.
Ventral surface: Rounded, lipped only slightly.
Lips: Slightly unequal.
Cavity: Flaring, somewhat elongated in the suture plane, stem indentation marks present occasionally.
*Depth.*—7/16" [11.1 mm.].
*Breadth.*—1 1/8" [28.6 mm.].
Base: Truncate, slightly cordate if viewed parallel to suture.
Apex: Rounded.
Pistil point: An inconspicuous Moderate yellow [87. m.Y] dot.
Stem: Medium.
*Average length.*—7/16" [11.1 mm.].
*Average width.*—3/32" [2.4 mm.].
Skin:
*Thickness.*—Medium.
*Surface.*—Smooth.
*Tenacity.*—Tenacious to flesh.
*Astringency.*—Only slightly astringent.
*Tendency to crack.*—Slight.
*Color.*—Dark reddish orange [38. d.rO] streaking over a Moderate yellow [87. mY] and Light yellow [86. l.Y] two-tone variegated background with Light yellow [86. l.Y] freckling observable only on the red portion of the plum.
*Surface bloom.*—Moderate.
Flesh:
*Color.*—Light yellow [86. l.Y] from skin to stone with no bleeding.
*Surface of pit cavity.*—Covered with very short Moderate yellow [87. m.Y] fibers.
*Amygdalin.*—Moderate to scarce.
*Juice.*—Abundant, rich.
*Texture.*—Firm, crisp.
*Fibers.*—Abundant, fine.
*Ripens.*—Evenly.
*Flavor.*—Predominantly plum flavor with a hint of apricot, slightly acidic and very sweet, typically 20 brix.
*Aroma.*—Slight.
*Eating quality.*—Excellent.

Stone

Type: Semi-freestone becoming freestone when fully mature.
Form: Oval.
Hilum: Narrow, oblong.
Base: Straight.
Apex: Acute with an average angle of 80 degrees.
Sides: Equal.
Surface: Rough surface with no grooves or ridges.
External color of stone: Moderate yellowish brown [77. m.yBr].
Pit wall color when cracked: Light brown [57. l.Br].
Cavity surface color: Deep yellowish brown [75. deep yBr].
Average pit wall thickness: 1/16" [1.6 mm.].
Average width: 11/16" [17.5 mm.].
Average length: 1" [25.4 mm.].
Average breadth: 3/8" [9.5 mm.].
Tendency to split: Moderate if exposed to frost during blooming season.
Kernel:
*Form.*—Oval.
*Pellicle color.*—Moderate yellowish brown [77. m.yBr].
*Skin color.*—Dark orange yellow [72. d.OY].
*Taste.*—Bitter.
*Viable.*—Yes.
*Average width.*—1/2" [12.7 mm.].
*Average length.*—5/8" [15.9 mm.].
*Amygdalin.*—Abundant.

Use

Market: Fresh market and long distance shipping.
Keeping quality: Very good. Fruit quality observed to remain in good condition in after 30 days in standard cold room at 36° Fahrenheit [2° Celsius].
Shipping quality: Excellent.
Resistance to insects: No unusual susceptibilities noted.
Resistance to diseases: No unusual susceptibilities noted.

Other Notes

Although the new variety of interspecific plum tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

I claim:

1. A new and distinct variety of interspecific plum tree, substantially as illustrated and described, that is most similar to its seed grandparent, 'Bradgreen' (U.S. Plant Pat. No. 8,498), by producing fruit that is globose in shape, acidic and sweet in flavor, firm in texture, and matures in mid August, but is distinguished therefrom by blooming about ten days later and by producing fruit that is two-tone red and yellow instead of purely green in skin color, that is semi-freestone rather than clingstone in type, that is less susceptible to skin scuffing, and that has a unique plum with a hint of apricot flavor.

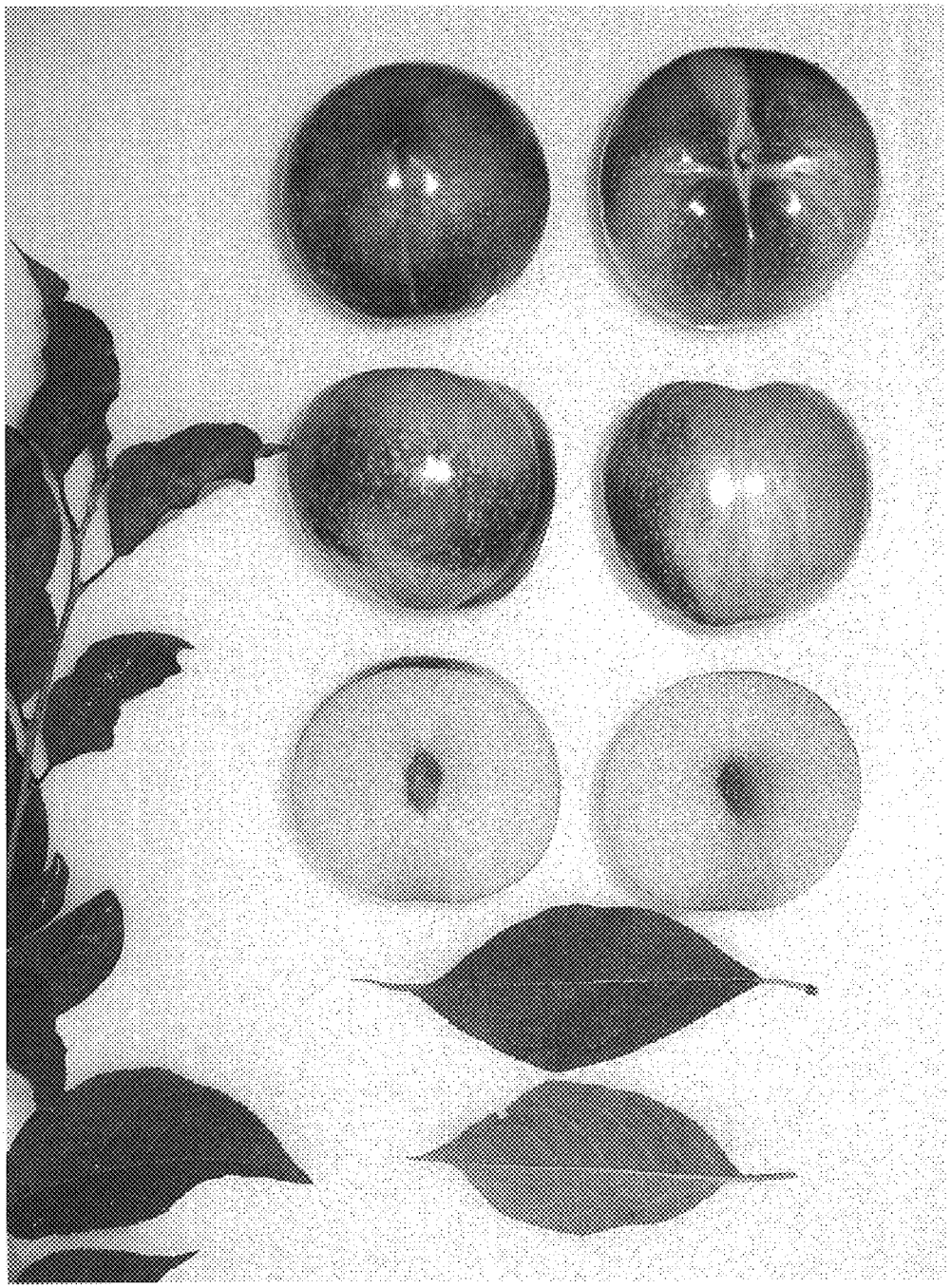

* * * * *